US010912716B2

(12) United States Patent
Yin et al.

(10) Patent No.: US 10,912,716 B2
(45) Date of Patent: Feb. 9, 2021

(54) MONITORING DEVICE FOR MONITORING THE DELIVERY AND TAKING OF MEDICATION PILLS AND A MONITORING METHOD

(71) Applicant: KONINKLIJKE PHILIPS N.V., Eindhoven (NL)

(72) Inventors: Bin Yin, Shanghai (CN); Sheng Jin, Shanghai (CN); Ying Zhang, Shanghai (CN); Mian Ding, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 132 days.

(21) Appl. No.: 16/225,871

(22) Filed: Dec. 19, 2018

(65) Prior Publication Data
US 2019/0183738 A1    Jun. 20, 2019

(30) Foreign Application Priority Data
Mar. 21, 2018 (EP) .................................... 18163007

(51) Int. Cl.
| A61J 7/04 | (2006.01) |
| G16H 20/13 | (2018.01) |
| A61J 7/00 | (2006.01) |

(52) U.S. Cl.
CPC ........... *A61J 7/0436* (2015.05); *A61J 7/0418* (2015.05); *A61J 7/0454* (2015.05); *A61J 7/0084* (2013.01); *A61J 7/0445* (2015.05); *A61J 7/0481* (2013.01); *A61J 2200/30* (2013.01); *G16H 20/13* (2018.01)

(58) Field of Classification Search
CPC .......................... G07F 17/0092; A61J 2200/30
See application file for complete search history.

(56) References Cited

U.S. PATENT DOCUMENTS

| 4,573,606 A | | 3/1986 | Lewis et al. | |
| 5,284,133 A | * | 2/1994 | Burns ................. | A61M 15/009 128/200.14 |
| 5,317,645 A | * | 5/1994 | Perozek ................. | G06M 11/00 209/522 |
| 6,286,714 B1 | * | 9/2001 | Pearson .................... | A61J 7/02 221/164 |
| 6,510,962 B1 | | 1/2003 | Lim | |
| 6,629,625 B1 | * | 10/2003 | Paczkowski .............. | G07F 9/02 221/2 |
| 2007/0023034 A1 | * | 2/2007 | Jongejan ............. | A61M 15/009 128/200.14 |
| 2007/0186923 A1 | * | 8/2007 | Poutiatine ........... | G06F 19/3462 128/200.14 |
| 2015/0286798 A1 | * | 10/2015 | Weber ................... | G06T 7/0012 348/143 |
| 2017/0300660 A1 | | 10/2017 | Ziv et al. | |
| 2017/0326033 A1 | * | 11/2017 | Kraft ...................... | G16H 20/13 |
| 2017/0354574 A1 | | 12/2017 | Feng et al. | |
| 2018/0296442 A1 | * | 10/2018 | Paz ........................ | G16H 50/20 |

FOREIGN PATENT DOCUMENTS

WO         0145059 A1    6/2001

* cited by examiner

*Primary Examiner* — Timothy R Waggoner

(57) ABSTRACT

A device is provided for monitoring the delivery and taking of medication pills by detecting both the passage of a pill and the covering of a pill outlet region, which is indicative of an active operation of the user to remove the pill from the pill outlet region. In this way, pill delivery can be monitored as well as an indication of actual pill taking.

13 Claims, 3 Drawing Sheets

MONITORING DEVICE FOR MONITORING THE DELIVERY AND TAKING OF MEDICATION PILLS AND A MONITORING METHOD

CROSS REFERENCE TO RELATED APPLICATIONS

This application claims the benefit of European Patent Application Number 18163007.0, filed Mar. 21, 2018 and PCT International Application Number PCT/CN2017/117422, filed Dec. 20, 2017, which are hereby incorporated by reference herein.

FIELD OF THE INVENTION

This invention relates to a device and method for monitoring the taking of pills, in particular forming part of, or being attached to, a pill dispensing unit.

BACKGROUND OF THE INVENTION

Complying with prescribed medication is crucial for chronic disease management at home. Poor compliance leads to suboptimal recovery, unnecessary deterioration, increased risk of hospital admission and eventually higher mortality and morbidity.

Electronic programmable pill dispensers are known for improving the medication compliance, for example by making prefilled drugs accessible according to a pre-programmed medication plan. The dispenser generates reminding signals and records the delivery of pills to the user so that historical information about the delivery of pills to the user is available.

Various methods are also known to make sure patients have actually taken their medication at the appropriate times. For example, for a pill dispenser which is tilted to cause a pill to be released, it is known to detect the tilt of the pill dispenser. It has also been proposed to monitor the patient instead, for example by analyzing their posture over time to detect pill taking activities, although this approach is difficult to implement in reality.

There remains the need for an easy-to-use pill dispenser which enables the delivery and taking of medication to be recorded automatically, but without introducing significant additional system complexity.

SUMMARY OF THE INVENTION

The invention is defined by the claims,

According to a first aspect of the invention, there is provided a monitoring device for monitoring the delivery and taking of medication pills, comprising:

a pill exit channel having a pill outlet region;

a detector located at the pill exit channel, for detecting the covering of the pill outlet region by a user and for detecting the passage of a pill past the detector, wherein a first type of detector signal is representative of covering of the pill outlet region and a second type of detector signal is representative of the passage of a pill; and a controller for storing, interpreting or transmitting the detector signals.

This device makes use of a monitoring device to monitor that pills have been dispensed along a pill exit channel and that the pill outlet region was actively engaged by the user, in particular the pill outlet region was covered by the user when removing the pill. A single detector generates an output which can discriminate between both situations. The device may be used as part of a system for checking that pills have been dispensed but also that they have actually been taken by a user of the system. This provides more accurate compliance information and thus enables personalized medication management.

The controller may perform signal analysis locally, or it may simply store or transmit the signals. In all cases, the signals are eventually interpreted to provide a report of the pill dispensing and pill taking history of the user of the device.

The monitoring device is in particular for use with, or as part of, a hand-held pill intake unit, and it is provided at the outlet of a pill dispensing station. In combination with a pill dispensing station, a drug intake assistant is provided, which may then function as a small portable drug container as well as a drug intake monitor.

The detector for example comprises a light source and a light detector.

A light source and detector provides a low-cost sensing approach. The detector may be designed so that the lips, mouth or fingers contacting the pill outlet region alter the detector signal in a first way and the passage of a pill alters the detector signal in a different way. Thus, the same detector may be used for both events. The detector signals may have characteristic amplitude or temporal features which enable identification of pill dispensing and pill taking.

The light detector is for example located adjacent the light source and is for detecting reflected light.

This provides a compact arrangement. One type of reflection (based on its amplitude and/or temporal characteristics) is caused by the lips, mouth or fingers and another type is caused by a passing pill.

The device may comprise a window in the pill exit channel in the line of sight of the light source.

When this window is uncovered, the light source light escapes (or has a first reflection characteristic), and when it is covered, there is a reflected signal (or a reflected signal with a second reflection characteristic), which can thus be detected. The pill for example provides a different reflection characteristic and typically for a shorter duration.

The controller (whether local or remote) is adapted to interpret the detector signals to discriminate between the passage of different types of pills.

Different types of pill may also give rise to different detector signal characteristics, for example different amplitude and/or different time durations. For example, for a fixed pill delivery speed, different sizes of pills will have different signal durations. Different color pills will for example have different reflection characteristics.

The device may comprise a high pass filter for filtering the detector signals.

In this way, step changes in detector signals (for example during the time that a pill is passing or during the time that the outlet is in use) are filtered to create pulses. The nature of these pulses then gives timing information which enables different events to be detected.

The device may further comprise a set of one or more physiological sensors PS (as shown in FIG. 2).

These sensors may be used when the device is in use, so that vital signs monitoring may also be conducted. They may be pulse rate, temperature and oxygen saturation.

In one set of examples, the pill exit channel is a mouthpiece. The device is then for monitoring within a system which is intended to deliver pills directly to the mouth of the user. The pill is for example delivered towards the pill outlet region, and it is then sucked out by the user from this location. Thus, the use of mouthpiece involves contact with the pill outlet region, rather than just tipping the pill into the hand of the user. The user may equivalently remove the pill by grasping a protruding portion between the fingers. The pill exit channel is designed so that such an action is also detected as covering of the pill outlet region.

The controller may be adapted to interpret the detector signals to discriminate between motion representative of insertion of the mouthpiece into the mouth of the user and the passage of a pill.

The monitoring device may be attachable to different types of pill delivery system, and then function as an add-on unit to provide additional monitoring functionality. Instead, the device may further comprise a chamber for storing medication pills. The device then comprises a combined pill storage, delivery and monitoring system. This enables the pill monitoring system to be designed for the specific pill chamber and dispensing unit.

Thus, the invention also provides a pill storage, delivery and monitoring system, comprising a chamber for storing medication pills, a monitoring system as defined above and a delivery unit for delivering pills from the chamber to the monitoring system.

The invention also provides a method for monitoring the delivery and taking of medication pills, comprising, during the passage of a pill from a chamber to a pill exit channel which leads to a pill outlet region of a pill dispensing device:

obtaining a first type of detector signal in response to the covering of the pill outlet region by a user;

obtaining a second type of detector signal in response to the passage of a pill; and interpreting the detector signals to provide a report of the pill dispensing and pill taking history of the user of the pill dispensing device.

The detector for example comprises a light source and a light detector.

The method may include interpreting the detector signals to discriminate between the passage of different types of pills. There may also be physiological sensing at the pill outlet region.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
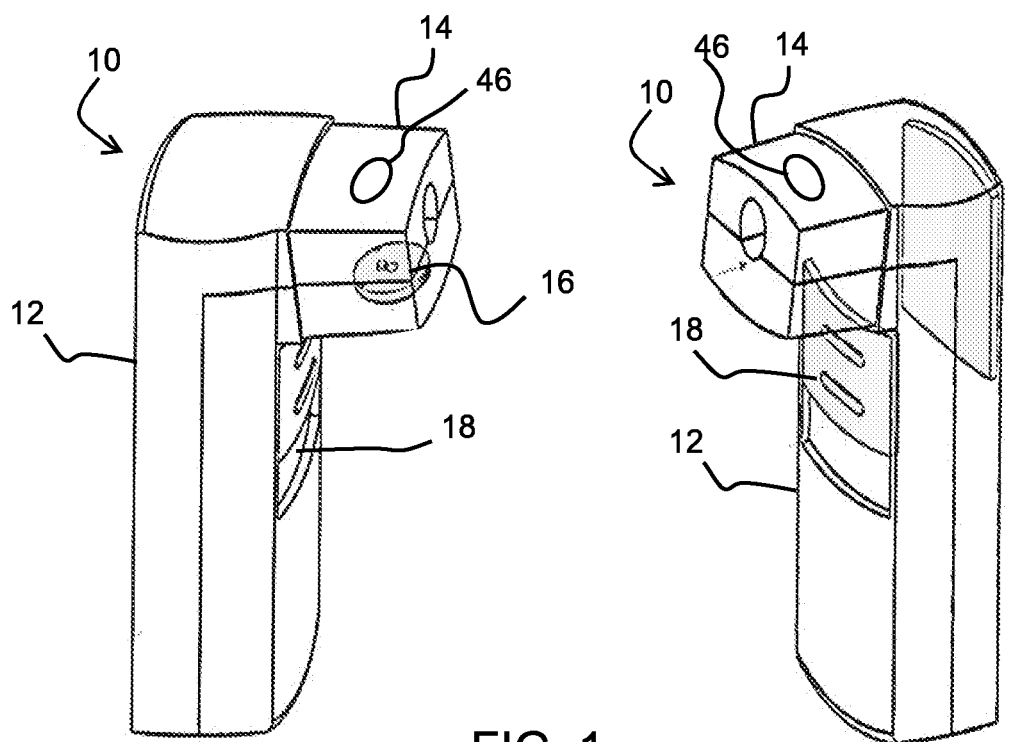
FIG. 1 shows a pill storage, delivery and monitoring system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a device for monitoring the delivery and taking of medication pills by detecting both the passage of a pill and the covering of a pill outlet region, which is indicative of an active operation of the user to remove the pill from the pill outlet region. In this way, pill delivery can be monitored as well as an indication of actual pill taking.

FIG. 1 shows two views of a pill storage, delivery and monitoring system 10.

The system comprises a pill delivery system 12, for storage and dispensing of pills to a pill monitoring device 14. The invention relates in particular to the monitoring device 14, and it may be attachable to different types of pill delivery system 12, and then function as an add-on unit to provide additional monitoring functionality.

The pill delivery system 12 preferably delivers one pill at a time to its outlet, and its outlet is connected to an inlet of the monitoring device 14. The pill passes a detector 16 when it advances to the outlet. A slider 18 is used to advance the pills to the outlet. FIG. 1 also shows a window 46, which is described further below, and performs part of the function of the detector 16.

The pill delivery system may take many different known forms. It is preferably a fully mechanical device having a mechanical delivery mechanism.

In one set of examples, the pills (of a particular size and shape for which the pill delivery system is designed) are loaded into the pill delivery system, and the pill delivery system stores them in an organized and ordered arrangement. Manual actuation of the pill delivery system then causes one pill from stored ordered arrangement to be delivered to the outlet. There may for example be a spring loaded magazine, wherein each actuation of the pill delivery system causes the magazine to advance by one location and as a consequence deliver a pill to the outlet of the pill delivery system.

In another set of examples, the pill delivery system may be loaded with a blister pack and it may be designed to peel back the blister and expel one pill at a time to the outlet. This may again be a fully manual process.

Other examples may make use of motorized pill delivery, for example electrically driving a magazine as described above, or rotating a blister pack spool, wherein the rotation causes peeling back of a blister layer.

As mentioned above, the pill delivery system preferably delivers one pill at a time, i.e. one pill for each user actuation. However, this is not essential. For example, the pill delivery system may be for delivery of different pills in a particular sequence, and there may be delivery of one pill of one type followed by two (smaller) pills of another type.

The pills may be non-spherical such as capsules or cylinders, and they may then have a particular orientation in which they are stored and dispensed. However, they may instead be spherical. This may enable a loose containment of the pills rather than storage in a magazine or blister pack.

The invention may be based on any known pill delivery system.

Figure 2:
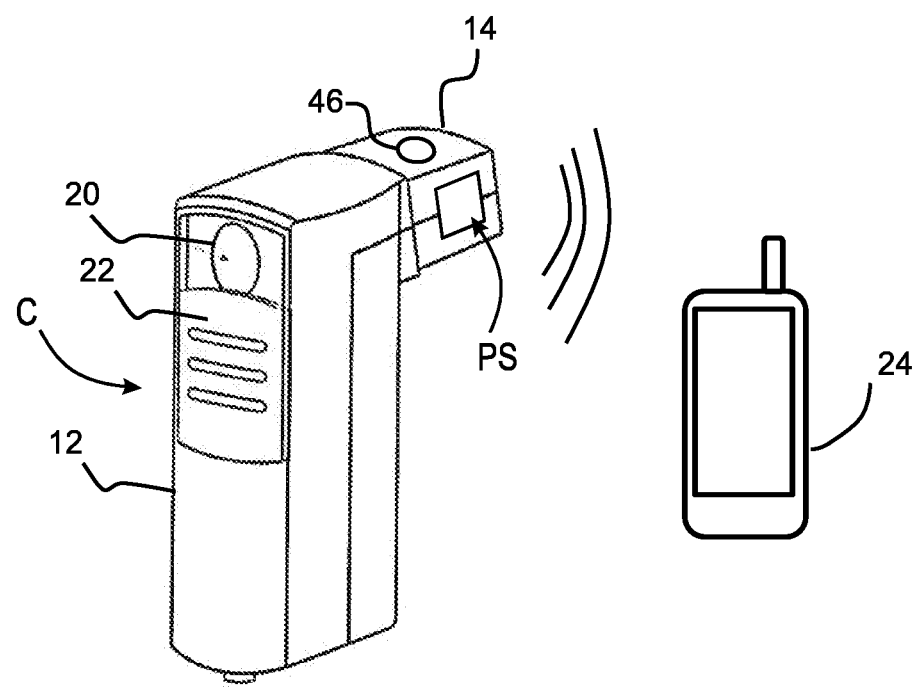
FIG. 2 shows another view of the system of FIG. 1.

FIG. 2 shows that the pill delivery system in this example has an entry opening 20 at a rear face with a slidable cover 22, where pills are introduced into chamber C one at a time. Thus, this design is a magazine type design, where actuation of the slider 18 advances the magazine by one pill position. Note that the delivery of pills into the entry opening 20 may be performed by the user, or a separate device may be provided for automatically loading the pills into the pill delivery system from another container which is supplied to the user in a filled state. For example, the user may purchase a cartridge which is loaded into the pill delivery system instead of loading pills one at a time.

The pill storage, delivery and monitoring system 10 communicates wirelessly with a remote device 24 such as a mobile telephone, or with a cloud server (not shown). The remote device 24 or the cloud server may then store and analyze data. The pill monitoring device 14 has a wireless communications module for this purpose. As an alternative, the communications capability may be part of the pill delivery system 12 when a fully integrated system is provided.

After the data analysis, a report of the pill dispensing and pill taking history of the user may be generated, the remote device 24 may present the report to the physician/caregiver or patient. Alternatively, the cloud server may transfer the report to a remote device such as a laptop, a mobile telephone or an electronic tablet of the physician/caregiver or the patient. Then, a poor medication compliance level or omission of a critical drug, the patient and/or his/her caregiver may then be alerted.

Figure 3:
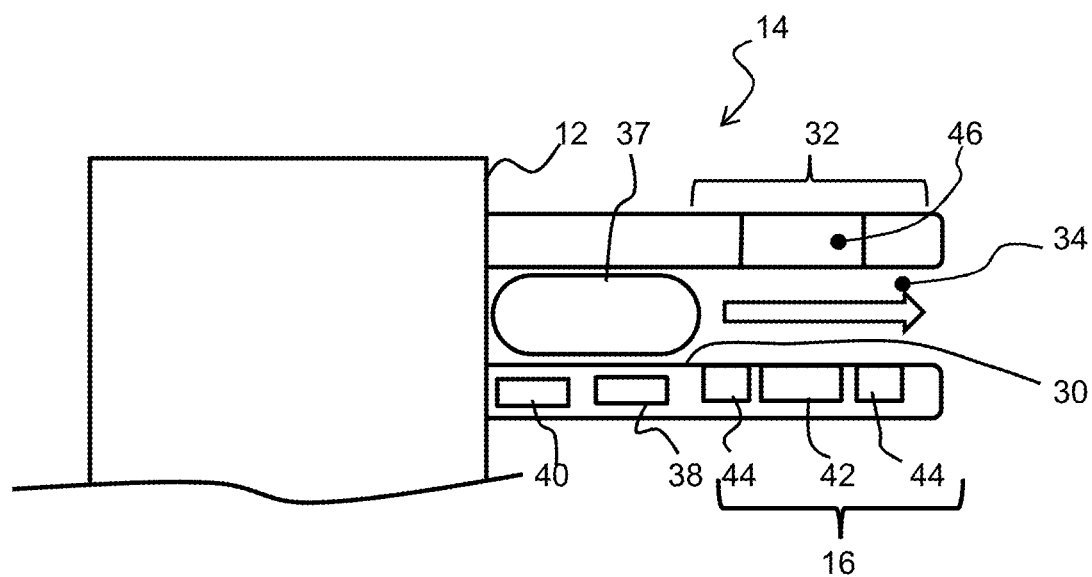
FIG. 3 shows the monitoring device used in the system of FIGS. 1 and 2 in more detail.

FIG. 3 shows the monitoring device 14 in more detail. It comprises a pill exit channel 30 having a pill outlet region 32. This output region is in the vicinity of the final pill outlet 34.

The detector 16 is located at the pill exit channel 30, for detecting the covering of the pill outlet region 32 by a user and for detecting the passage of a pill 37 past the detector 16.

A single detector is used for detecting these two different events, and characteristics of the detector signal are used to differentiate between pill passage detection and detection of the covering of the pill output region 32. Thus, there is a first type of detector signal representative of covering of the pill outlet region and a second type of detector signal representative of the passage of a pill 37.

There is a controller 38 for storing, interpreting or transmitting the detector signals via a wireless communications module 40. The controller 38 may be a standalone processor. The controller 38 may be integrated with the detector 16. The controller 38 may simply collect detector signals for wireless communication so that all data processing is performed externally, or else some or all of the required data processing may take place at the controller 38. The processing is able to provide a report of the pill dispensing and pill taking history of the user of the device.

This device makes use of a monitoring device to monitor that pills 37 have been dispensed along the pill exit channel 30 and that the pill outlet region was actively engaged by the user. When a part of the pill outlet region is covered by the user, this is detected.

In the preferred example as shown, the pill outlet region 32 is covered by the lips and/or mouth in use when removing the pill, but it is equally possible that the user is able to remove the pill by hand.

The detector 16 in the example shown comprises a light source 42 and a light detector 44. This provides a low-cost sensing approach. The light detector 44 is located adjacent the light source (for example formed as an annulus around the light source) and is for detecting reflected light. Different types of reflected signal then may represent different events, in particular internal passage of a pill or external covering of the pill outlet region 32. These differences for example relate to amplitude and/or temporal and/or spectral characteristics.

Opposite the light source 42, there is provided a window 46 in the pill exit channel 30 in the line of sight of the light source 42. When this window 46 is uncovered, the light source light escapes (or has a first reflection characteristic), and when it is covered, there is a reflected signal (or a reflected signal with a second reflection characteristic), which can thus be detected.

There are various possible designs for the window 46. In combination, the detector 16 and the window 46 are able to distinguish between covering and not covering of the window and also presence and absence of a pill. The window may simply be an opening, so that the light source light escapes from the window when it is uncovered, so that there is only ambient light sensing when the window is uncovered. There is instead sensing of reflected light from the light source when the window is covered. The ambient light and the reflected light source light have different light characteristics including intensity and color, which can thus be discriminated. For example, the light source light may be brighter but with a narrower spectrum than the ambient light, and hence covering of the window results in increased reflection of this light. Covering of the window may alternatively or additionally be detected based on a drop of detected ambient light.

Similarly, reflection of light source light from a pill, which is closer to the detector, will have a different light characteristic in terms of color and/or intensity.

As will be seen below, in addition to considering light intensity and/or spectrum, temporal characteristics may also be used to interpret the detected signals.

The window may instead be a transparent or translucent material. It may also be partially reflective, as long as a change in reflection is observable when the window is covered.

Figure 4:
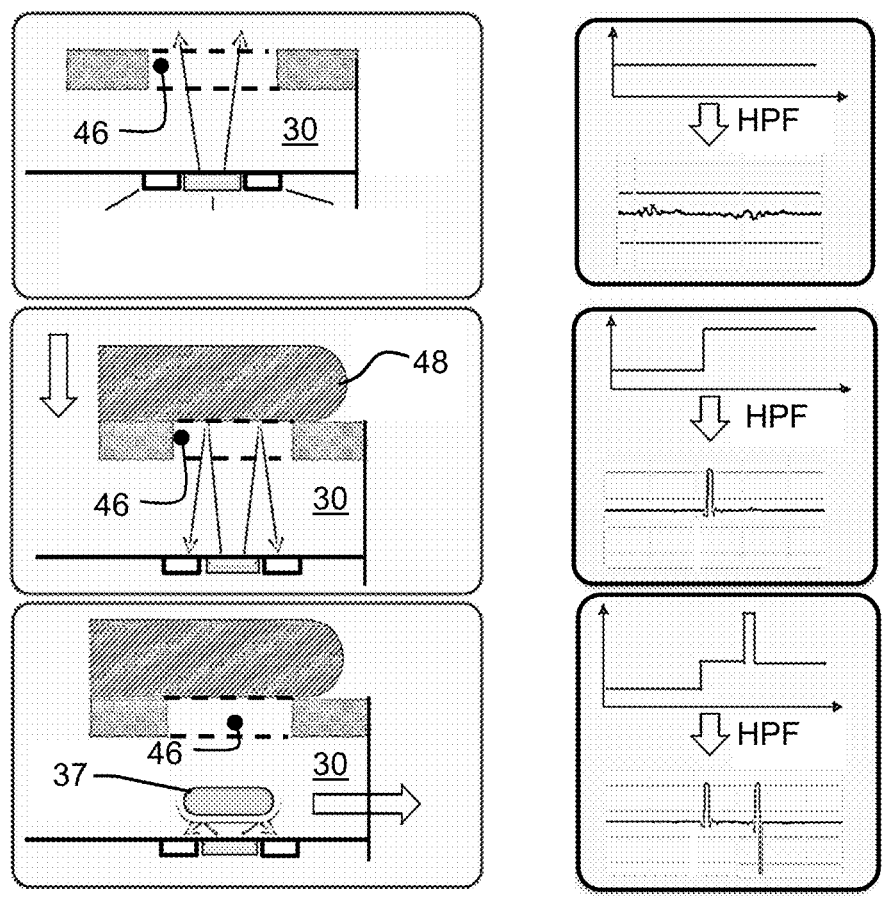
FIG. 4 is used to explain the operation of the monitoring device.

FIG. 4 is used to explain the operation of the monitoring device based on one possible detection approach.

The left images show the condition inside and outside the pill exit channel 30. The right images show the detector signal over time as well as a high pass filtered version.

The top row shows an empty pill exit channel 30 with nothing covering the window 46. The detection signal is constant giving only baseline noise in the high pass filtered version The middle row shows the window being covered by a lip 48 of the user when the pill exit channel 30 is inserted into the mouth of the user. The detected light intensity increases when the window 46 is covered by the lip (or finger) of the user, due to a shortened light path. There is thus a step increase in detected light, and when high pass filtered, this gives a pulse.

The bottom row shows first the covering of the window 46 by the lip of the user, and then the passage of a pill 37. There is an initial increase in the detector signal due to increased reflection from the window, then a further increase when the pill arrives, and a reduction when the pill has passed. When high pass filtered, this gives a first pulse, and then two more closely spaced pulses corresponding to the passage of the pill.

The in-mouth part of the outlet region is designed to ensure that the window 46 is covered when the mouthpiece is used.

It can be seen from the description above that the timing of pulses is representative of the event taking place, and in particular the nature of the motion involved. The controller may thus discriminate between motion representative of insertion of the mouthpiece into the mouth of the user (which may be a relatively slow operation which remains effective for a relatively long time) and the passage of a pill (which may be a relative fast operation which remains effective for a relatively short time).

Figure 5:
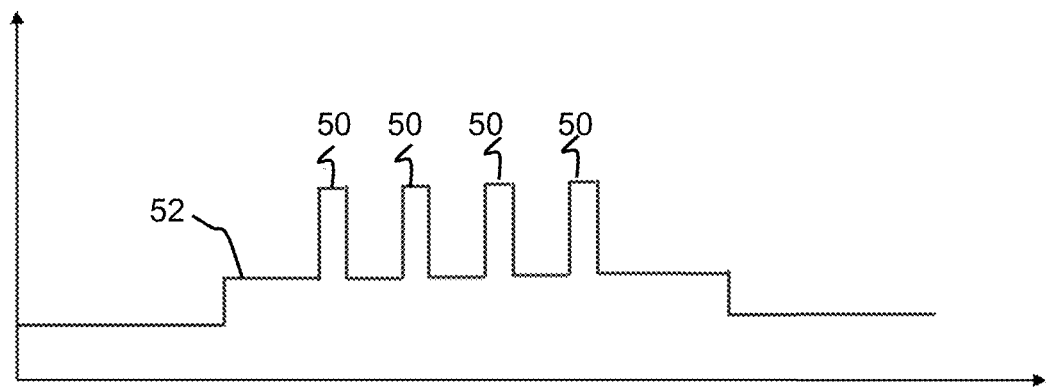
FIG. 5 shows the detector signal when multiple pills have passed along the pill exit channel.

FIG. 5 shows the raw detector signal when multiple pills have passed along the pill exit channel 30. There are multiple consecutive pulses 50 of the received light intensity signal superposed over the longer pulse 52 representing the covering of the window. This means a number of pills being taken can be counted.

Furthermore, the color, shape and size of the pills will determine how the light is reflected, scattered and absorbed, so the resultant light intensity signal and characteristics may also provide information about the type of a certain pill. The information is modulated into the width, height and general morphology of a pulse.

Thus, it can be seen that the raw sensor data and/or the high pass filtered version may be of interest in determining different events.

Figure 6:
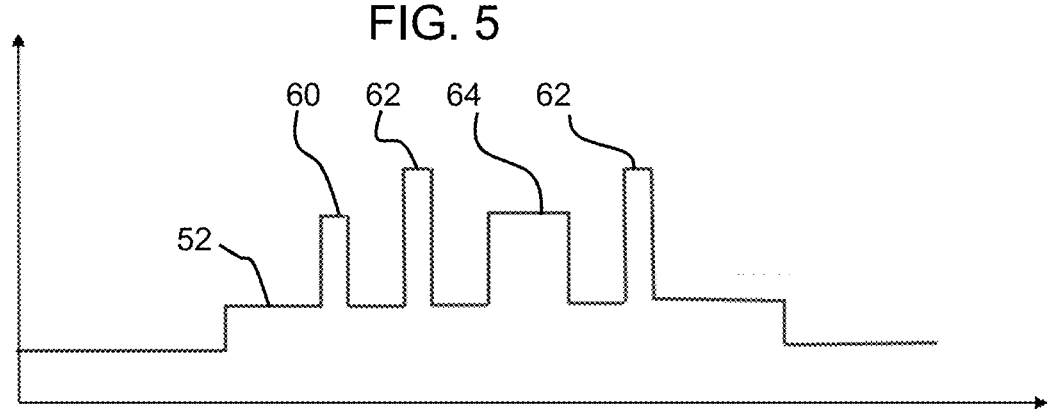
FIG. 6 shows a detector signal when multiple pills of different sizes and reflection characteristics have passed along the pill exit channel.

FIG. 6 shows a detector signal when multiple pills of different sizes and reflection characteristics have passed along the pill exit channel 30.

A first pulse type 60 has low intensity representing for example a relatively absorptive color and a small duration representing a small size. A second pulse type 62 has high intensity representing for example a relatively reflective color and a low duration representing a small size. A third pulse type 64 has low intensity representing for example a relatively absorptive color and a large duration representing a large size. These are again superposed over the longer pulse 52 representing the covering of the window. This means a number of pills being taken of different types can be counted.

A signal analysis algorithm may then be pre-trained based on various types of pills, which is then able to record both the quantity and type of pills being taken.

The pill dispensing and consumption information can be collected via a wired or wireless connection to a mobile device as explained above, or to a central pill dispenser, to allow systematic management of the medication of a user. For instance, in the case of a poor medication compliance level or omission of a critical drug, the patient and/or his/her caregiver may then be alerted.

Since the unit will be placed in contact with the user, for example partly placed in the mouth touching the lip of the use, other vital signs may be measured using the same and/or additional sensors, such as pulse rate, temperature and oxygen saturation. These measurements serve as important information for the holistic management at home of, for instance, a patient with a chronic disease.

Figure 7:
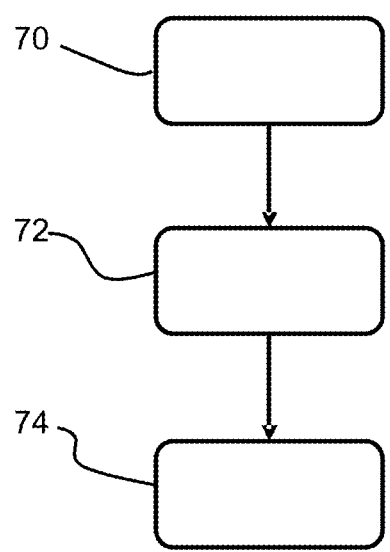
FIG. 7 shows a method for monitoring the delivery and taking of medication pills.

FIG. 7 shows a method for monitoring the delivery and taking of medication pills, comprising, during the passage of a pill from a chamber to a pill exit channel which leads to a pill outlet region of a pill dispensing device:

step 70 of obtaining a first type of detector signal in response to the covering of the pill outlet region by a user;

step 72 of obtaining a second type of detector signal in response to the passage of a pill; and step 74 of interpreting the detector signals to provide a report of the pill dispensing and pill taking history of the user of the pill dispensing device.

This invention can be used in the management of chronic patients outside hospitals, for instance, cardiovascular disease patients after hospitalization. It also finds application in management solutions for high risk populations (such as with hypertension and/or diabetes).

Only one example of detector has been shown above.

An optical system may be based on reflection as shown above, or on transmission from one location to another. For example a light source may be on one side of the pill exit channel and the sensor may be on the other side. The user's lip or finger will block external light entering the channel and thus reduce the light detected, and a pill will block the light travelling across the channel, thereby reducing the detected light further.

Other sensors are possible, such as based on capacitance sensing, where external contact as well as the passage of a proximate pill give a different sensor response.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A monitoring device for monitoring the delivery and taking of medication pills, comprising:
   a pill exit channel having a pill outlet region, the pill outlet region having a window;
   a detector located at the pill exit channel, the detector configured to detect a covering of the window of the pill outlet region by a user and the passage of a pill past the detector, wherein a first type of detector signal is representative of the covering of the window of the pill outlet region and a second type of detector signal is representative of the passage of the pill; and
   a controller for storing, interpreting or transmitting the detector signals.

2. The device as claimed in claim 1, wherein the detector comprises a light source and a light detector.

3. The device as claimed in claim 2, wherein the light detector is located adjacent the light source and is configured to detect reflected light.

4. The device as claimed in claim 1, wherein the controller is adapted to interpret the detector signals to discriminate between the passage of different types of pills.

5. The device as claimed in claim 1, comprising a high pass filter configured to filter the detector signals.

6. The device as claimed in claim 1, further comprising a set of one or more physiological sensors.

7. The device as claimed in claim 1, wherein the pill exit channel is a mouthpiece.

8. The device as claimed in claim 7, wherein the controller is adapted to interpret the detector signals to discriminate between motion representative of insertion of the mouthpiece into the mouth of the user and the passage of a pill.

9. A pill storage, delivery and monitoring system, comprising:
   a chamber configured to store medication pills;
   a monitoring system as claimed in claim 1; and a delivery system configured to deliver pills from the chamber to the monitoring system.

10. A method for monitoring the delivery and taking of medication pills, comprising, during the passage of a pill from a chamber to a pill exit channel which leads to a pill outlet region of a pill dispensing device:
   obtaining, from a detector having a light source and a light detector, a first type of detector signal in response to the covering of a window in the pill outlet region by a user, wherein the window is in a line of sight of the light source;
   obtaining, from the detector, a second type of detector signal in response to the passage of a pill; and
   interpreting the detector signals to provide a report of the pill dispensing and pill taking history of the user of the pill dispensing device.

11. The method as claimed in claim 10, comprising interpreting the detector signals to discriminate between the passage of different types of pills.

12. The method as claimed in claim 10, further comprising providing physiological sensing at the pill outlet region.

13. A monitoring device for monitoring the delivery and taking of medication pills, comprising:
   a pill exit channel having a pill outlet region;
   a detector located at the pill exit channel, the detector configured to detect the covering of the pill outlet region by a user and the passage of a pill past the detector, wherein a first type of detector signal is representative of the covering of the pill outlet region and a second type of detector signal is representative of the passage of the pill, wherein the detector comprises a light source and a light detector;
   a window in the pill exit channel in a line of sight of the light source; and
   a controller for storing, interpreting or transmitting the detector signals.

* * * * *